(12) United States Patent
Karapetyan

(10) Patent No.: US 7,220,123 B1
(45) Date of Patent: May 22, 2007

(54) DEVICE FOR REGISTRATION OF THE DENTAL BITE

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 346 days.

(21) Appl. No.: 10/999,278

(22) Filed: Nov. 30, 2004

(51) Int. Cl.
*A61C 9/00* (2006.01)

(52) U.S. Cl. .............................. 433/37; 433/43; 433/44

(58) Field of Classification Search ................ 433/37, 433/38, 45, 71, 80, 39, 43, 44; 132/323, 132/324
See application file for complete search history.

(56) References Cited

U.S. PATENT DOCUMENTS

| | | | |
|---|---|---|---|
| 1,411,156 A * | 3/1922 | Bowen | 433/45 |
| 1,411,505 A * | 4/1922 | Northwood | 433/45 |
| 1,461,209 A * | 7/1923 | Bridges | 433/46 |
| 2,860,414 A * | 11/1958 | Brant | 433/43 |
| 3,574,259 A * | 4/1971 | Jones | 433/38 |
| 4,439,147 A | 3/1984 | Magill et al. | |
| 4,602,905 A | 7/1986 | O'Keefe, III | |
| 4,689,010 A * | 8/1987 | Wolfe | 433/38 |
| 5,076,785 A * | 12/1991 | Tsai | 433/46 |
| 5,154,609 A | 10/1992 | George | |
| 5,190,062 A * | 3/1993 | Rafaeli | 132/323 |
| 5,282,678 A * | 2/1994 | Teufel et al. | 312/221 |
| 5,733,118 A * | 3/1998 | Pankuch et al. | 433/38 |
| 6,527,549 B1 * | 3/2003 | Berzins | 433/45 |
| 6,582,931 B1 | 6/2003 | Kois et al. | |
| 6,835,065 B1 * | 12/2004 | Wise | 433/38 |
| 2003/0138754 A1 * | 7/2003 | DiMarino et al. | 433/37 |

* cited by examiner

*Primary Examiner*—Melba N. Bumgarner
*Assistant Examiner*—Jonathan Werner

(57) ABSTRACT

An improved device for registration of dental bite provides a possibility to make accurate impression of the patient's dental bite and includes the first portion and second portion. The first portion comprises a first mouth portion and a first handle portion, and the second portion includes a second mouth portion and a second handle portion. Each of the first mouth portion and second mouth portion are generally of half-U-shaped configuration, and in the coupled position form the U-shaped configuration. Also, the device comprises the connector located in the handle portions of the first portion and second portion respectively, and which includes a first connecting portion located on the first handle portion and the second connecting portion located on the second handle portion.

1 Claim, 3 Drawing Sheets

DEVICE FOR REGISTRATION OF THE DENTAL BITE

FIELD OF THE INVENTION

This invention relates to dental devices, tools for orienting a patient's bite, capturing or registering in bite registration material the tilt or slant of the occlusal plane of the patient's teeth and, more particularly, to a devices, instruments for facilitating the fabrication of functional orthodontic appliances by providing accurate alignment of the teeth preparatory to the fabrication process.

BACKGROUND OF THE INVENTION

Orthopedic appliances have been increasingly used in both children and adults for correcting improper alignment of the teeth. The known orthodontic appliances, which are molded to accurately conform to the teeth and jaws of the individual user, have proven to be especially valuable in correcting malocclusions such as overbite and underbite, and open bite, where the upper and lower incisors do not contact one another.

It is also known in the fabrication of orthopedic appliances for use in closed bite cases, the typical first step is to obtain what is commonly termed a "construction bite" and/or occlusion. The occlusion is corresponded to the proper alignment of the jaw and teeth with the finished orthopedic appliance in position within the patient's mouth. As known, that in order to achieve the optimum correction of the misalignment, it is required that the occlusion be obtained as accurately as possible. When an accurate construction bite has been obtained a wax mold inserted between the posterior teeth will be imprinted with such construction bite, and can thereafter be used in the fabrication, such as by molding, of the finished orthopedic appliance.

In obtaining occlusion, dentists and dental technicians have sometimes relied on visual sighting and manual manipulation of the jaws to properly align the teeth. Additionally, some dentists have used tongue depressors inserted between the upper and lower incisors to achieve proper spacing therebetween, together with visual alignment of the midpoints of the upper and lower incisors. That is, with an increasing number of orthodontic appliances, the upper and lower incisors must be spaced apart to accommodate biting surfaces of the appliances themselves, thereby requiring accurate vertical, horizontal, and rotational alignment of the teeth preparatory to the construction bite. Although visual sighting of the midline of the upper and lower incisors have proven satisfactory in achieving rotational alignment, such method, whether alone or in combination with manual manipulation of the jaws, has not proven satisfactory in achieving accurate horizontal and vertical alignment.

For example, the bite-taking device disclosed in U.S. Pat. No. 4,439,147 provides the registration of the occlusion. This device includes an elongated handle having a ridge running from its outer end to its inner end, an enlarged portion, biting panel, and stops. The enlarged portion and stops have curved surfaces corresponding to the curvatures of the incisors and generally extending the width of the incisors. Biting panel extends a length in excess of the thickness of the incisor teeth, i.e., the length from enlarged portion to stops. Surfaces of stops are adapted to abut the rear portions of the upper and lower incisors whereas in its alternate use surfaces or enlarged portion are adapted to abut the outer surfaces of the upper and lower incisors. The biting panel is inserted into the patient's mouth and brought upward against the upper incisors just in front of one of the stops. The patient is then directed to gently bite down until the lower incisors contact the undersurface of biting panel, after which the handle is pulled gently outwardly to bring the upper and lower incisors into abutting relationship with stops, while at the same time visual sighting is made of the upper and lower incisors to achieve accurate midline adjustment. The surfaces of stops have been brought into abutting relationship with the inner surfaces of the upper and lower incisors.

The temporomandibular joint articulates the mandible to the temporal bone of the skull. If the dental patient portion of the temporomandibular joint is misaligned or if the joint or the interposed disc is damaged or destroyed pain and altered function may result. One technique used to relieve joint pressure and reposition the members of the joint involves the construction of a removable intraoral appliance or splint into which the upper and lower teeth fit in such a manner as to realign and reposition the members of the temporomandibular joint in an attempt to relieve joint pressure, provide relaxation of the jaw muscles and allow healing of the joint.

A splint is typically molded from a thermoplastic or thermosetting polymer and contains on its upper and lower surfaces a reverse image or impression of the upper teeth and the lower teeth. Stone models or casts are made from these impressions of the upper and lower teeth. These casts must then be positioned or registered relative to each other so as to achieve a desired relationship in the temporomandibular joint. As known, the splints have been made by first taking separate impressions of the upper and lower teeth utilizing conventional techniques. An intraocclusal bite record is then usually made by placing a relatively thin sheet of wax or other bite registration material between the patient's teeth and having the patient bite in the desired jaw relationship. This procedure involves a separate step utilizing the registration material which is subsequently interposed between the dental casts or models of the teeth to align the models in the desired relationship. This conventional step of relating dental casts with a separate interposed bite registration material for the purpose of producing splints, or for other occlusal therapy, introduces inaccuracies because inherent distortion of the wax or other bite registration material, especially from temperature changes, may result in an inaccurate mounting or relationship of the patient's dental casts. The multiple steps involved in handling the separate bite registration material also lead to additional distortion of the relationship between the mounted casts.

As described in the known sources, mounting the lower dental cast to the upper cast requires a separate step which is a facebow transfer. A facebow is positioned on the patient's head relative to the axis-orbital plane which relates the location of the upper dental arch to the temporomandibular joint. The facebow is then transferred to an articulator, a machine used to simulate jaw function. The model made from the impression of the upper teeth can then be positioned on the articulator utilizing the facebow. This separate step also introduces the possibility of distortion of the mounting. Thereafter, the model made from the impression of the lower teeth is positioned against the upper model using the intraocclusal bite record. Completion of these separate steps and mounting of the dental casts on the articulator yields a rigid mechanical analog of an individual's jaw movements and relationships.

For instance as known, if it is desired to make a splint in which the patient's lower jaw is moved two millimeters forward of its normally closed position to relieve pressure on the temporomandibular joint, the model of the lower teeth is moved forward relative to the model of the upper teeth and affixed at the new position. A splint is then produced from the repositioned location of the models of the upper and lower teeth. As one might surmise, this repositioning can introduce several inaccuracies into the splint. As a result, when a splint is fitted to a patient's teeth, a significant amount of time and effort may be required in order to obtain a final accurate relationship of the paired temporomandibular joints and the upper and lower teeth relative to the splint. This same registration technique described herein is applicable to recording jaw positions and relationships for fabrication of removable orthodontic appliances, for relating complete dentures, for mounting dental casts for diagnostic purposes including bite adjustments and for fabrication of single or multiple units of fixed or removable prosthetics.

The one of the known instruments by U.S. Pat. No. 4,602,905 describes the dental registration device comprising a double-sided impression tray having an anterior reinforcing enlargement through which first and second channels extend in an anterior/posterior direction. The first channel is shaped to receive a flat registration tab onto which can be positioned a deformable registration material, such as ordinary dental wax. The upper channel removably receives a reciprocator rod. A reciprocator knob threadably engages the reciprocator rod. The registration tab and the reciprocator knob coact so, that selective rotation of the knob will selectively reciprocate the registration tab in the registration channel. The impression tray has two symmetrical U-shaped ridges on the upper side of a septum and mirror image ridges extending downwardly from the lower side of the septum. The first set of ridges are spaced equidistantly from each other and with the septum define an upper impression cavity. Similarly, the lower ridges in conjunction with the septum form a lower impression cavity. The notch is extended downwardly from the upper ridge of the anterior ridge and is positioned at the anterior central end of the ridge. The flange extends forwardly from the anterior ridges adjacent the plane of the septum. The flange also extends rearwardly from the anterior ridges and lies beneath the septum. The registration channel has a rectangular cross section for receiving registration tab and the deformable registration material. The registration tab comprises a rectangular tab that slidably engages the upper surface of the registration channel and the coplanar lower surface of the reinforcement flange. The rectangular tab has an anterior extension that extends first downwardly from the anterior edge of the tab, then extends forwardly and terminates in an upwardly oriented flange. The second channel is positioned above the lower channel and has in a semicircular cross section. The posterior portion of the channel carries a downwardly extending nib, which in conjunction with an annular channel in the rod secures the rod in the channel in a predetermined position. The anterior end of the rod carries a cylindrically shaped threaded portion. Between the threaded portion and the posterior end of the rod are located a plurality of axially spaced indicia running in a circumferential direction relative to the rod. The reciprocator knob has an internal bore that is threaded to receive and engage the threaded portion of the rod.

In some construction of any rigid dental device that contacts both the upper and lower teeth, models of the patient's upper and lower dentition must be positioned on a dental articulator. It is important that they be related to each other in the same relationship as existed in the patient's mouth. Most functional orthodontic appliances are designed to keep the lower jaw forward. Therefore, the models on the articular must be positioned with the lower model forward relative to the upper model.

The most common way of transferring the dental relationship in the mouth to the articulator is with a simple wax bite. The dentist softens a block of wax with heat and inserts it between the patient's upper and lower teeth. The dentist then guides the jaw to the desired position and tells the patient to hold it there while the wax cools and hardens. The models of the patient's upper and lower teeth then can be correctly related to each other by fitting them into the indentations in the wax. The models, with the wax between them, are then attached to the articulator. This is done in a manner that will allow the wax bite to be discarded and still allow the articulator, which simulates jaw movements, to open and close back to the wax bite position.

The relationship of the mandible to the maxilla is determined by the relative positions of the incisal edges of the lower to upper central incisor teeth.

The U.S. Pat. No. 5,154,609 describes the dental bite registration device including the upper assembly incorporated the upper platform and a measuring arm. At the internal end of the upper platform is the impression platform with gripper holes to help secure the impression material on the platforms. (In this description the term "internal" refers to inside the mouth or toward the inside of the mouth, and "external" refers to outside the mouth or toward the outside of the mouth). The upper teeth indention is formed on the superior side of the upper platform by a notch which separates the upper internal block from the upper external block.

At the external end of the upper platform is the shank which connects with the measuring arm by its male portion of the snap lock. The most internal (proximal) end of the measuring arm is connected to the upper platform by its female portion of the snap lock. The most external border of the measuring arm is the measurement point which relates to the scale of the lower assembly.

The upper assembly fits within the lower assembly by inserting the measuring point in the internal (proximal) end of the channel. At the internal end of the lower assembly on the inferior side, the lower teeth indention is formed by a notch between the lower internal block and the lower external block.

The clamp, as a separate part, is either removably or permanently affixed to or near the middle of the length of the channel. The locking screw secures the anteroposterior relationship of the upper to lower assembly by compressing the measuring arm against the floor of the channel. At the internal end of the upper platform is the impression platform with gripper holes to secure the impression material on the platforms. At the external end of the impression platform is the upper teeth indention which is formed by a notch which separates the upper internal block from the upper external block. At the external end of the upper platform is the shank, which connects with the measuring arm by its male portion of the snap lock. The measuring arm is connected to the upper platform by its female portion of the snap lock. The connected measuring arm and upper platform are encased in the channel of the lower assembly in which they can freely slide anteroposteriorly. At or near the middle of the charnel is the clamp which encircles the lower assembly and the encased measuring arm. The locking screw is turned to compress the measuring arm against the floor of the channel, making it immobile.

As well known in mounting dental casts to an articulator, it is necessary to position the cast in the same relation to each other as the teeth in the patient's mouth as well as being orientated or related to the patient's hinge axis. In accomplishing that, impressions of the patient's occlusion (bite) are made in impression material positioned on a flat bite fork which is clamped between the patient's upper and lower teeth.

While the cast is held in that position, it is secured by dental plaster to a mounting plate attached to the upper frame of the dental articulator. Once the upper cast is mounted, the lower cast can be secured to the articulator by utilizing the upper cast as a guide along with an interocclusal record.

The U.S. Pat. No. 6,582,931 describes the dental-facial analyzer comprising a bite fork or plate, a pair of wings and the central portion which includes an elongated straight slot that extends forwardly from the center of the bite fork and opens to the front edge or, forward portion of the face bow. A disk-shaped holder, which includes grooves on its sides is sized to slide within the slot. The holder is formed with a central hole sized to receive a vertical indicator rod. This positions the rod perpendicular to the flat bow. One or more tubular markers slides on the upper and the lower end of the rod. A thumb screw fixes the rod relative to the holder.

The assembly also includes an upper index tray and a lower index tray. The upper index tray includes four downwardly extending pins or projections sized to fit within four mating holes formed in the bite fork. The projections are long enough such that they protrude through the bite fork and fit within four mating holes in the lower index tray. The upper index tray and lower index tray are also provided, with a number of small holes for receiving bite registration material such as impression compound. The lower frame of a dental articulator, which includes a vertical frame member topped by a pair of balls. The ball centers define a hinge axis. A horizontal lower frame member is connected to the lower portion of the vertical member and is supported on its forward end by a leg. A mounting platform assembly is mounted on a magnetic base plate secured to the lower frame member by a fastener.

While these known systems are relatively accurate, they are expensive, complex, require many different steps of the bite registration procedure, and comprise many components, the controllable means which are used for the tightening purposes (e.g. the screws to tighten), etc. As a result, many dentists (dental technicians) do not use such instruments. The most of the dental practitioners would utilize the greatly simplified dental articulator with the more simplified procedures for obtaining patient occlusion information with Also, the bite fork of the described instruments need to be sterilized before each use.

All described prior arts are expensive and in some way have the same deficiency, that is a complexity.

Thus, there is a great need in the art for the improved not complex and not expensive device for registration of dental bite, providing simplified manufacturing (technological) process.

OBJECT AND ADVANTAGES OF THE INVENTION

Accordingly, several objects and advantages of the present invention are to provide convenient, effective not complex and not expensive device for registration of dental bite.

It is another object of the invention to eliminate necessity to mold-in the impression supporting material.

It is still another object of the invention to reduce the complicity of the manufacturing technological process.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

An improved device for registration of dental bite provides a possibility to make accurate impression of the patient's dental bite.

An improved device for registration of dental bite includes the first portion and second portion. The first portion comprises a first mouth portion and a first handle portion, and the second portion includes a second mouth portion and a second handle portion. The first mouth portion and a second mouth portion can be used separately in the disconnected position for the bite impression registrations for example, only left or right side of the mouth, or be coupled to each other for the entire mouth bite impression registration. Each of the first mouth portion and second mouth portion are generally of half-U-shaped configuration, and in the coupled position form the U-shaped configuration. Also, the device comprises the connection means located in the handle portions of the first portion and second portion respectively. The connection means includes a first connecting portion located on the first handle portion and the second connecting portion located on the second handle portion.

DESCRIPTION OF THE PREFERRED EMBODIMENTS

Herein the description of an improved device for registration of dental bite will be done in statics (as if the components of the improved device are suspended in the space) with description of their relative connections to each other. The description of the functional operations of an the improved device for registration of dental bite will be done hereinafter.

Figure 1:
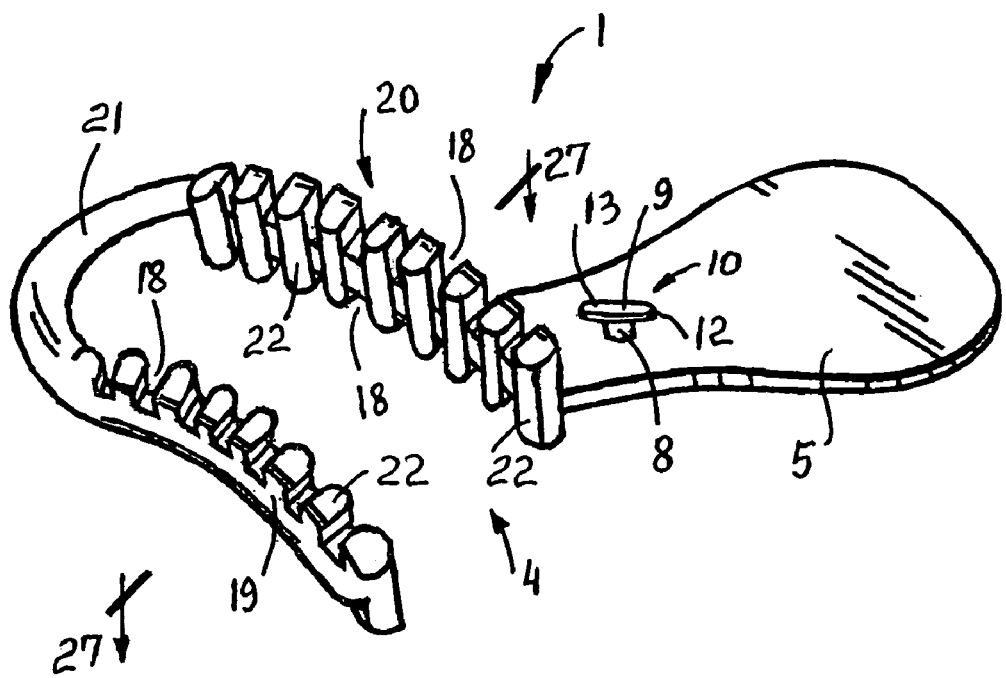
FIG. 1 is a spatial view of the first half-portion (the first portion) of the improved device for registration of dental bite.
Figure 2:
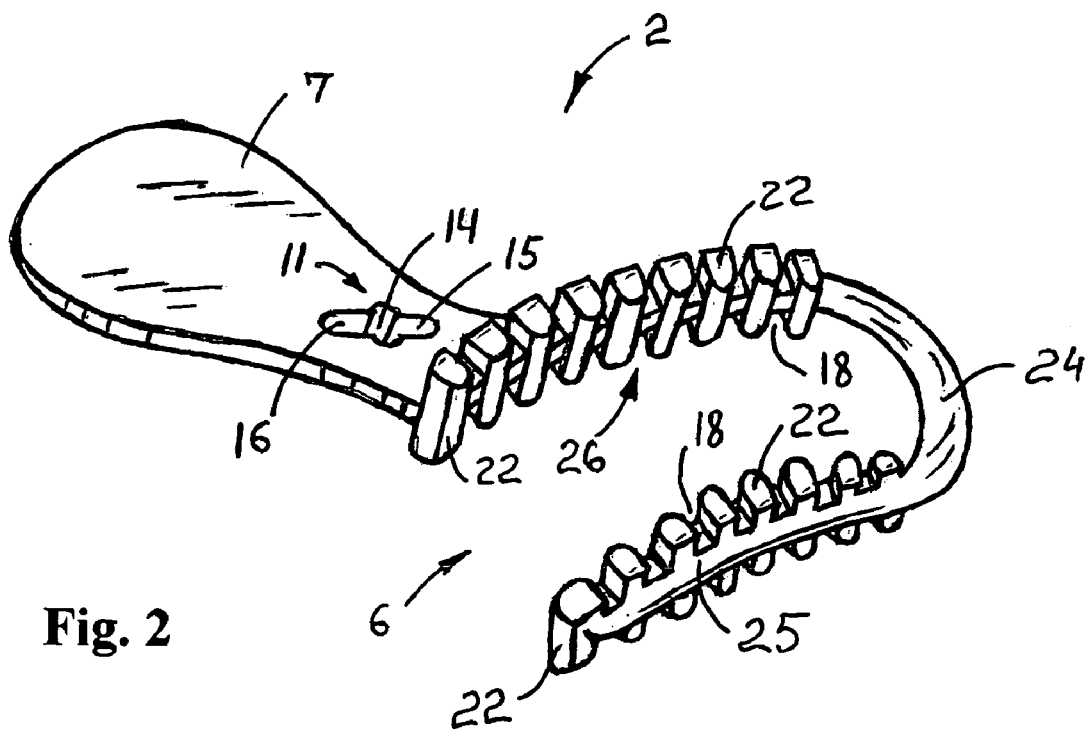
FIG. 2 is a spatial view of the second half-portion (the second portion) of the improved device for registration of dental bite.

An improved device for registration of dental bite, referring to FIG. 1, includes a first portion 1, a second portion 2. The first portion 1 comprises a first mouth portion 4 and a first handle portion 5. The second portion 2 (see FIG. 2) includes a second mouth portion 6 and a second handle portion 7. The first mouth portion 4 and a second mouth portion 6 can be used separately in the disconnected position for the bite impression registration, for example, only left or right side of the mouth, or coupled to each other can be used for the entire mouth bite impression registration. Each of the first mouth portion 4 and second mouth portion 6 are generally of half-U-shaped configuration, and in the coupled position form the U-shaped configuration. The U-shaped configuration and an appropriate dimensions of the mouth portion of the improved device for registration of dental bite provides the best fit in the mouth of a patient for bite impression treatment purposes. Generally, a U-shaped bite fork or plate is sized to mate with a patient's teeth or gums at the time of occlusion (the jaws are clamped on the impression compound). The first portion 1 and second portion 2 are coupled to each other by a connection means 3 located in the handle portions 5 and 7 of the first portion 1 and second portion 2 respectively, as shown in FIGS. 1, 2. The connection means 3 provides the locking coupling (see FIG. 4) of the first 1 and 2 portions when it is necessary in order to provide the registration of the entire mouth bite.

Figure 3:
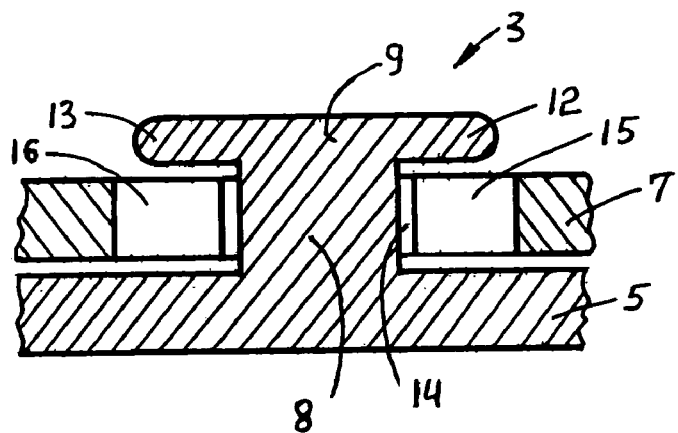
FIG. 3 is a cross-sectional view of the connection means in the connecting/disconnecting position.
Figure 4:
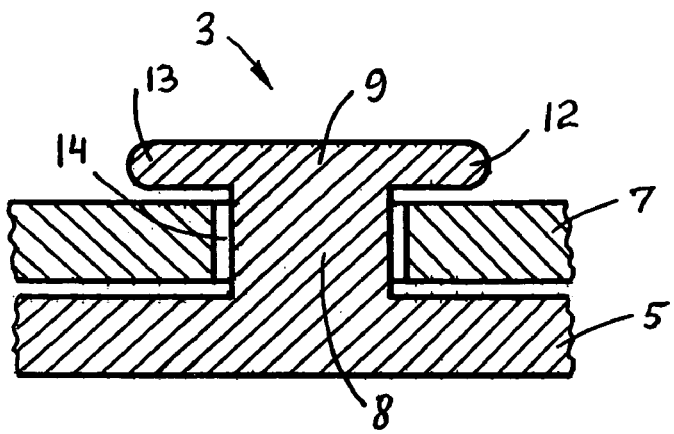
FIG. 4 is a cross-sectional view of the connection means in the locked position.

As shown in FIGS. 1–4, the connection means 3 comprises a first connecting portion 10 located on the first handle portion 5 and the second connecting portion 11 located on the second handle portion 7. The first connecting portion 10 includes a cylindrical portion 8 rigidly connected by its lower part to the first handle portion 5 (e.g. connected by screw or rivet /not shown/ or glued to each other by a reliable glue /not shown/, etc.) or can be extended of the first handle portion 5. The upper part of the cylindrical portion 8 is rigidly connected to the horizontal portion 9 (e.g. by reliable glue, screw /not shown/, etc.). The cylindrical portion 8 and horizontal portion 9 can be made (molded) of an entire (solid) piece. The horizontal portion 9 includes the first wing 12 and the second wing 13 located at 180° to each other, as shown in FIGS. 1, 3, 4.

The second connecting portion 11 includes an aperture 14 with the first openings 15 and second opening 16. The position of the aperture 14 with the first openings 15 and second opening 16 is located in the second handle portion 7 in such manner, that it will appropriately fit the first connecting portion 10, as it is shown in FIGS. 3, 4. The coupled first 1 and second 2 portions form U-shaped mouth portion (not shown) of the improved bite registration device.

Figure 6:
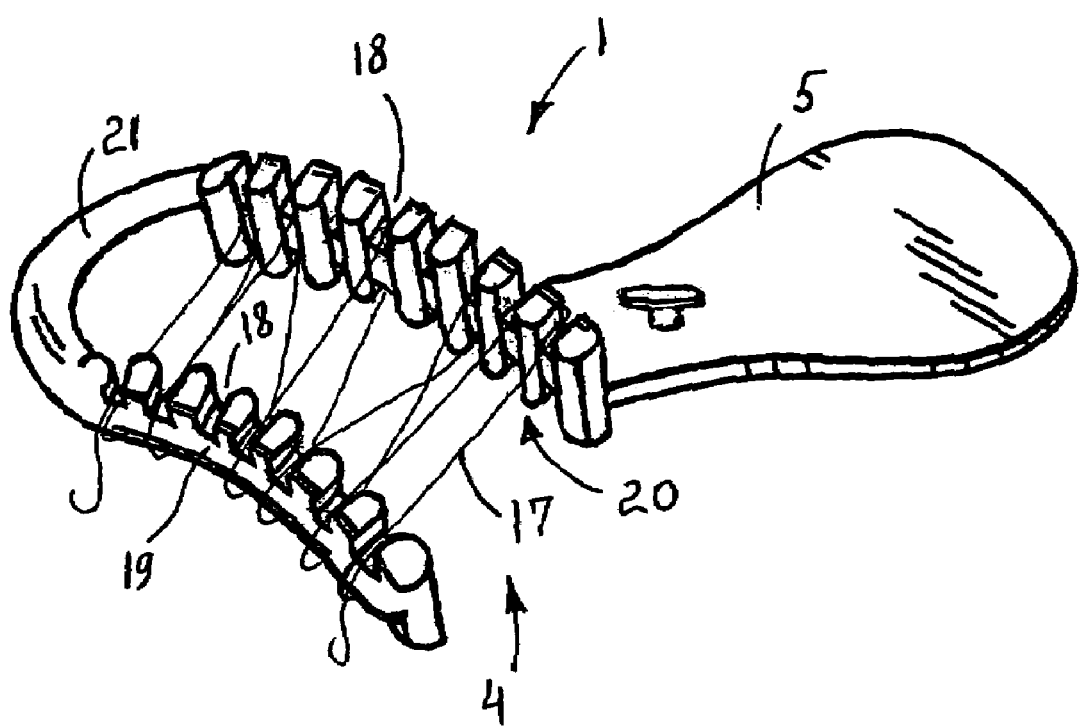
FIG. 6 is a simplified representation of the supporting thread installation.

The impression compound (impression material) is supported (fixed/prevented of the vertical bias/movement) in the first mouth portion 4 by a reliable first thread 17 wound on the first mouth portion 4, as shown in FIG. 6. The first thread 17 is passes through the slots 18 located at the first front portion 19 and first rear portion 20 of the first mouth portion 4. The first thread 17 can be connected (e.g. glued, tied, etc.) to the first mouth portion 4 in any manner. Also, the first thread 17 can be wound on the first mouth portion 4 in any manner considering the purpose to support (to hold) the impression material between the inner sides of the first front portion 19 and first rear portion 20 of the first mouth portion 4. Symmetrically for the second mouth portion 6, the impression compound is supported in the second mouth portion 6 by a reliable second thread (not shown) wound on the second mouth portion 6, and second mouth portion 6, for example, analogically with the first mouth portion 4. The second thread can in the same manner pass through the analogous slots 18 located at the second front portion 25 and second rear portion 26 of the second mouth portion 6. The second thread can be connected (e.g. glued, tied, etc.) to the second mouth portion 6 in any manner or in the same manner as it is described for the first mouth portion 4. Also, the second thread can be wound on the second mouth portion 6 in any manner considering the purpose to support (to hold) the impression material between the inner sides of the second front portion 25 and second rear portion 26 of the second mouth portion 6.

Figure 5:
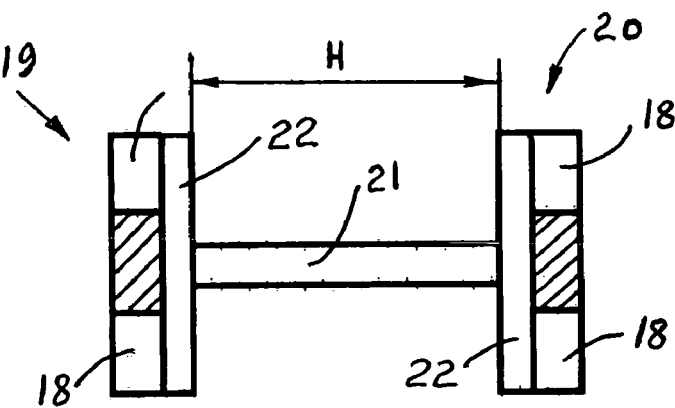
FIG. 5 is a simplified cross-sectional view 27—27 of the mouth portion.

The different tension of the threads provide the different distance "H" (see FIG. 5) between front portion 19 and rear portion 20, and front portion 25 and rear portion 26 of the appropriate mouth portions respectively. Such additional control of the distance "H" provides the convenient adjustment (alignment) of each mouth portion width for the different dental patients. The slots 18 can be of any width (e.g. more narrow then the width shown in FIGS. 1, 2). The first bridge 21 provides connection of the first front 19 and first rear 20 portions of the first mouth portion 4, and the second bridge 24 provides connection of the second front 25 and second rear 26 portions of the second mouth portion 6. The projections 22 (see FIGS. 1, 2, 5) are intended to fix the impression compound in the horizontal plane (not shown) of the mouth portions, preventing horizontal bias/movements. The bridges of either one half-portion and the appropriate front and rear portions, and handle can be made of one solid piece (e.g. molded, etc.).

All components and means of the improved device for registration of dental bite can be of any reasonable color, size, form and/or configuration, and made of any flexible reasonable and reliable material, for example, such as plastic (e.g. acrylic resin, polyvinyl chloride or polyamide polymer, which can be formed into the desired shape by conventional molding or casting operations), or flexible metal (that can be withstandable for the repeated sterilization procedures), etc, and should be not hazardous for human health.

Thus, an improved device for registration of dental bite provides convenient, effective and non-expensive device for use in making dentures.

CONCLUSION, RAMIFICATION AND SCOPE

Accordingly the reader will see that, according to the invention, I have provided a device for registration of dental bite, providing convenient, effective not complex and not expensive dental bite registration device for making an accurate and authentic teeth. An improved device has various possibilities, considering activities of the dental practice.

While the above description contains many specificities, these should be not construed as limitations on the scope of the invention but as exemplification of the presently-preferred embodiments thereof. Many other ramifications are possible within the teaching to the invention. For example, an improved device for registration of dental bite eliminates the necessity of the dentist's staff (technicians) to use any complex apparatus to register the patient's dental impression.

The present invention has been described in accordance with a preferred embodiment and variations thereof. One of ordinary skill will be able to effect changes to the disclosed embodiments, various substitutions of equivalents, and other alterations without departing from the broad concepts disclosed.

Thus, the scope of the invention should be determined by the appended claims and their legal equivalents, and not by examples given.

What is claimed is:

1. A device for registration of dental bite comprising
a first portion including a first mouth portion and a first handle portion, wherein said first mouth portion is of a half-U-shaped configuration;

a second portion including a second mouth portion and a second handle portion, wherein said second mouth portion is of an another half-U-shaped configuration;

a first front portion of said first mouth portion connected by a first bridge to a first rear portion of said first mouth portion, wherein said first bridge connects the left sides of said first front portion and said first rear portion, and wherein a right side of said first rear portion is connected to said first handle portion;

a second front portion of said second mouth portion connected by a second bridge to a second rear portion of said second mouth portion, wherein said second bridge connects the right sides of said second front portion and said second rear portion, and wherein a left side of said second rear portion is connected to said second handle portion;

a connection means intended for coupling of said first portion with said second portion providing U-shaped configuration of the mouth portion of the coupled first and second portions, and wherein said connection means includes a first connecting portion located on said first handle portion of said device for registration of dental bite, wherein said first connecting portion comprises a horizontal portion including a first wing and a second wing;

a cylindrical portion coupled with said horizontal portion;

a second connecting portion located in said second handle portion of said device for registration of dental bite, wherein said second connecting portion comprises a first opening intended for the passage of said first wing of said horizontal portion of said first connecting portion;

a second opening intended for the passage of said second wing of said horizontal portion of said first connecting portion;

an aperture the diameter of which is slightly bigger than the diameter of said cylindrical portion of said first connecting portion to provide the passage and pivotability of said cylindrical portion into said aperture;

a first thread coupled with said first mouth portion;

a second thread coupled with said second mouth portion;

at least two slots located in said first front portion of said first mouth portion and at least two appropriate slots appropriately located in said first rear portion of said first mouth portion, and at least two adequate slots located in said second front portion of said second mouth portion and at least two appropriate slots appropriately located in said second rear portion of said first mouth portion, wherein a width of said slots are bigger of the width of said first thread and width of said second thread, wherein the slots are intended for winding of an appropriate thread through the appropriate slots, and wherein a tension of the threads provides a desirable distance between said first front portion and said first rear portion of said first mouth portion and between said second front portion and said second rear portion of said second mouth portion.

* * * * *